(12) United States Patent
Gasco

(10) Patent No.: US 6,238,694 B1
(45) Date of Patent: May 29, 2001

(54) PHARMACEUTICAL COMPOSITION IN FORM OF SOLID LIPIDIC MICROPARTICLES SUITABLE TO PARENTERAL ADMINISTRATION

(76) Inventor: Maria Rosa Gasco, Lungo Po Antonelli, 207, 10153 Torino (IT)

( * ) Notice: Subject to any disclaimer, the term of this patent is extended or adjusted under 35 U.S.C. 154(b) by 0 days.

(21) Appl. No.: 09/445,603

(22) PCT Filed: May 27, 1998

(86) PCT No.: PCT/EP98/03110

§ 371 Date: Dec. 7, 1999

§ 102(e) Date: Dec. 7, 1999

(87) PCT Pub. No.: WO98/56362

PCT Pub. Date: Dec. 17, 1998

(30) Foreign Application Priority Data

Jun. 12, 1997 (IT) .............................................. MI97A1385

(51) Int. Cl.[7] .................................................... A61K 9/127
(52) U.S. Cl. ............................ 424/450; 424/426; 264/4.1
(58) Field of Search ..................................... 424/450, 426, 424/455; 264/4.1

(56) References Cited

U.S. PATENT DOCUMENTS 5,744,155 * 4/1998 Friedman et al. .................... 424/434
5,985,354 * 11/1999 Mathiowitz et al. ............... 427/2.21

FOREIGN PATENT DOCUMENTS

2091152 A1 * 9/1994 (CA) .
WO 526666
A1 * 2/1993 (WO) .

* cited by examiner

Primary Examiner—Thurman K. Page
Assistant Examiner—Liliana Dinola Baron
(74) Attorney, Agent, or Firm—Hedman & Costigan, P.C.

(57) ABSTRACT

A method of making a pharmaceutical composition containing a drug and solid lipidic microparticles, which are suitable for parenteral administration and resistant to phagocytosis by macrophage, is described.

5 Claims, No Drawings

PHARMACEUTICAL COMPOSITION IN FORM OF SOLID LIPIDIC MICROPARTICLES SUITABLE TO PARENTERAL ADMINISTRATION

The present application is the national stage filing of and claims priority to International Application No. PCT/EP98/03110, filed May 27, 1998 and Italian Application Serial No. MI97A001385.

PRIOR ART

Solid lipidic microspheres having a diameter lower than one micrometer obtained for example adding a mixture formed by water, a surfactant and a co-surfactant to a melt lipidic substance and dispersing the obtained microemulsion in cold water are known.

Microspheres of this kind and the relating preparation process are described for example in the European Patent 0526666B1.

Said microspheres are important carriers of drugs, however in the case of parenteral administration they may show a significative limitation.

In fact the presence of the lymphoreticular system causes a fast clearance of the lipidic particles due to the effect of the phagocytosis by the macrophages, from which a limitation to the parenteral use of said microspheres as transport systems of drugs derives.

SUMMARY

Now we have found a pharmaceutical composition in form of lipidic solid microparticles shape which allow to overcome the drawbacks of the prior art. Said microparticles have an average diameter lower than one micrometer and a polydispersion index ranging from 0.10 to 0.50 and they are characterized in that they contain a drug and one or more substances suitable to sterically stabilize the microparticies.

The process for the preparation of said microparticles includes:

a) heating a lipidic substance at a temperature at least equal to its melting point;

b) heating a mixture comprising water, a surfactant and a co-surfactant at a temperature at least equal to the melting point of the lipidic substance of the step a);

c) putting the lipidic substance of the step a) in contact with the mixture of the step b) obtaining a microemulsion;

d) dispersing the micro-emulsion obtained in the step c) in cold water;

e) washing the dispersion of the step d) with distilled water by diafiltration, and it is characterized in that at the end of the step c) a drug and one or more substances suitable to sterically stabilize said microparticles are added.

The composition according to the present invention turns out to be suitable for the parenteral administration.

DETAILED DESCRIPTION OF THE INVENTION

The characteristics and the advantages of the pharmaceutical compositions in form of solid lipidic microparticles shape suitable to parenteral administration according to the present invention will be mainly shown during the following detailed description.

For the preparation of said microparticles a lipidic component, or a mixture of lipidic components, is melt-heated; separately an aqueous solution containing one or more surfactants and one or more co-surfactants is prepared and the resulting solution is heated at a temperature at least equal to the melting point of said lipidic component or mixture of lipidic components; this solution is mixed under mild stirring with said lipidic component or said mixture of lipidic components, obtaining a microemulsion; to the so obtained microemulsion a drug and a substance suitable to sterically stabilize the microparticles are added; the so obtained mixture is poured in water having a temperature ranging from 2 to 10° C. under stirring obtaining the desired composition in the shape of well dispersed lipidic microspheres; the dispersion is washed several times with distilled water by diafiltration with the TCF 2 SYSTEM and finally it is concentrated to 100–120 g/ll or freeze-dried. As an alternative embodiment said microemulsion is added to a mixture consisting of water, surfactant, co-surfactant and optionally lipidic substances heated at a temperature such that all the lipidic substances are obtained in the melted state; to the so obtained mixture a drug and one or more substances suitable to sterically stabilize the microparticles are added; the so obtained mixture is poured in water having a temperature ranging from 2 to 10° C. under stirring and then it is washed and treated as above described.

The lipidic components used in the process of the present invention are selected from the group consisting of:

triglycerides such as for example trilaurin, tricapriloin, tristearin, tripalmitin; diglycerides as for example dipaimitin and distearin; fatty acids from $C_{12}$ to $C_{22}$ as for example lauric acid, myristic acid, palmitic acid and stearic acid and their esters with polyalcohols as the propylene glycol; alcohols as ethanol, lauryl, myristic, cetyl, stearyl alcohols; cholesterol and its esters such as cholesterylpalmitate, cholesterylbutyrate and cholesterylbenzoate.

The surfactants are selected from the group consisting of:

sodium cholate, sodium deoxycholate, sodium glycocholate, sodium taurocholate, sodium taurodeoxycholate, lecithin and phospholipides and their hydrogenated forms, Tween 20, Tween 40, Tween 80, Span 20, Span 40, Span 60, Span 80, emulsifiers such as gelatin.

The co-surfactants are selected from the group consisting of:

bile salts as sodium taurocholate, alcohols and glycols having low molecular weight as for example butanol, hexanediol, propylene glycol and hexanol, fatty acids having low molecular weight as for example butyric acid and caproic acid, esters of the phosphoric acid and benzyl alcohol.

Drugs suitable for the compositions according to the present invention are for example hydrocortisone, testosterone, 5-fluorouracil, thymopentin, somatostatin, LHRH and its homologues, propanolol, enteral vasoactive peptide and methotrexate.

Substances suitable to sterically stabilize the microparticles according to the present invention are the dipalmitoyl phosphatidylethanolamine-PEG, the PEG-stearate and the fatty acids, from the myristic one to the docosanoic one, pegoylated by methyl ether of polyethylene glycol (PEG. Me M. W. 750–2000).With the term "pegoylated" is to be intended "esterified with monomethyl ether of polyethylene glycol".

Other substances suitable to sterically stabilize the microparticles according to the present invention are for example the diacylphosphatidylethanolamines pegoylated with PEG. Me (M. W. 750–2000) and the biodegradable polymers having average molecular weight ranging from 2000 to 50,000 (such as polyglycolactates, polylactates) pegoylated with PEG. Me (M. W. 750–2000). In the preparation of the microemulsion according to the present invention the various substances are used in the following proportions:

- lipidic components ranging from 5 to 30% and preferably from 10 to 20% by weight of the total weight;
- water ranging from 40 to 70% and preferably from 55 to 65% by weight of the total weight;
- surfactants ranging from 8 to 30% and preferably from 12 to 20% by weight of the total weight;
- co-surfactants ranging from 0 to 15% and preferably from 3 to 7% by weight of the total weight.

The amount of substances suitable to sterically stabilize the microparticles is ranging from 0.04 to 2.5% by weight with respect to said microemulsion and the amount of drug is ranging from 0.1 to 10% by weight with respect to said microemulsion.

The amount of water for the dispersion of the microemulsion ranges from 1 to 10 volumes of water per volume of microemulsion.

The drug content with respect to the lipidic substance is ranging from 0.4 to 12% by weight and the content of the substance suitable to sterically stabilize the microparticles with respect to the lipidic substance is ranging from 0.8 to 8% by weight.

Operating according to the present invention a pharmaceutical composition in form of particles having an average diameter lower than one micrometer and in particular ranging from 40 to 150 nm, and a polydispersion index ranging from 0.10 to 0.50 is obtained. Said pharmaceutical composition may be used successfully in the parenteral administration.

In fact the captation of the compositions according to the present invention by the macrophages turns out to be markedly decreased with respect to the compositions of the prior art, as it is shown in the experimentation on the murine macrophages reported below.

Pharmacological Experimentation

A culture of murine macrophages has been realized and the phagocytosis assay has been carried out in presence of the compositions according to the invention in comparison to a composition of the prior art. Macrophages 1774.A1 have been cultured in monolayers at 37° C., in 5% $CO_2$, in RPMI 1640 supplemented with 5% fetal bovine serum.

The cells have been incubated for 24 hours at 37° C. in a 24 well culture plate and washed. The adherent cells have been further incubated in DME-F12 with 10% fetal bovine serum.

Assays have been carried out adding to the culture the products of the Examples 1 and 4 (products without substance suitable to sterically stabilize the microparticles) and the products of the Examples 2, 3, 5 and 6 (containing a substance suitable to sterically stabilize the microparticles) respectively. The description of the Examples is reported below.

Said products have been added in an amount equal to 1.26 mg per ml of culture. After periods of incubation from 2.5 to 90 minutes the phagocytosis has been determined in resuspended cells, measured as function of the fluorescence intensity ($\lambda$ EX=545 and $\lambda$ EM=580).

In the Table 1 the captation by the macrophages of the products of the Example 2 (2a, 2b and 2c) is reported in comparison with the product of the Example 1 after various times, expressed as % of the dose on a million cells.

TABLE 1

| Time | % Captation by the macrophages | | | |
|---|---|---|---|---|
| (min) | Example 1 | Example 2a | Example 2b | Example 2c |
| 10 | 30 | 3 | 4 | 5 |
| 20 | 32 | 5 | 5 | 10 |
| 60 | 37 | 6 | 6 | 10 |
| 90 | 33 | 3 | 6 | 10 |

In Table 2 the captation by the macrophages relative to the products of the Example 3 (3a, 3b and 3c) is reported in comparison with the product of the Example 1.

TABLE 2

| Time | % Captation by the macrophages | | | |
|---|---|---|---|---|
| (min) | Example 1 | Example 3a | Example 3b | Example 3c |
| 10 | 30 | 0 | 0 | 0 |
| 20 | 32 | 1 | 2 | 2 |
| 60 | 37 | 2 | 2 | 3 |
| 90 | 33 | 2 | 2 | 3 |

In the Table 3 the captation by the macrophages relative to the products of the Example 5 (5a, 5b and 5c) is reported in comparison with the product of the Example 4.

TABLE 3

| Time | % Captation by the macrophages | | | |
|---|---|---|---|---|
| (min) | Example 4 | Example 5a | Example 5b | Example 5c |
| 10 | 39 | 5 | 6 | 10 |
| 20 | 44 | 5 | 7 | 12 |
| 60 | 44 | 6 | 7 | 12 |
| 90 | 38 | 6 | 6 | 11 |

In the Table 4 the captation by the macrophages relative to the products of the Example 6 (6a, 6b and 6c) is reported in comparison with the product of the Example 4.

TABLE 4

| Time | % Captation by the macrophages | | | |
|---|---|---|---|---|
| (min) | Example 4 | Example 6a | Example 6b | Example 6c |
| 10 | 39 | 3 | 3 | 3 |
| 20 | 44 | 4 | 4 | 6 |
| 60 | 44 | 3 | 3 | 5 |
| 90 | 38 | 2 | 2 | 3 |

The data of the Tables reported above show that the compositions according to the present invention allow to markedly reduce the captation of the microparticles by the macrophages.

For illustrative aim the following preparation Examples of the composition according to the present invention are reported.

EXAMPLE 1 (Comparison)

200 mg of stearic acid are melt-heated at about 70° C.

A mixture consisting of: 120 mg of Epikuron 200 (L. Meyer), as surfactant, 330 mg of sodium taurodeoxycholate, as co-surfactant, 2 ml of an aqueous solution containing 10 mg/ml of thymopentin and 7.5 mg of Rhodamine B used as fluorescent probe is heated at about 70° C. Said mixture is added to said stearic acid under mild stirring obtaining a clear micro-emulsion at about 70° C. Then the microemulsion is poured in water at a temperature about equal to 3° C. in a 1:5 ratio by volume under mechanical stirring.

A dispersion of microparticles has been so obtained which has been washed for three times with distilled water by diafiltration with TCF2 Systems (Amicon, Grace, Danvers-USA) and concentrated to 110 g/l. The obtained microparticies had an average diameter equal to 80 nanometers and a polydispersion index equal to 0.16.

EXAMPLE 2

Example 1 has been repeated with the difference that dipalmitoyl phosphatidylethanolamine-PEG (DPPE-PEG) has been also added to the said microemulsion respectively in the amounts equal to 0.2% (Example 2a), 0.4% (Example 2b) and 0.7% (Example 2c) with respect to the microemulsion.

The average diameter of the obtained microparticles and the polydispersion index are reported in the following Table.

| Example | Average diameter (nanometers) | polydispersion index |
|---------|-------------------------------|----------------------|
| 2a | 85 | 0.18 |
| 2b | 90 | 0.22 |
| 2c | 95 | 0.25 |

EXAMPLE 3

The Example 1 has been repeated with the difference that PEG stearate has been added to the said microemulsion respectively in the amounts equal to 0.15% (Example 3a), 0.30% (Example 3b) and 0.55% (Example 3c) with respect to the microemulsion.

The average diameter of the obtained microparticles and the polydispersion index are reported in the following Table.

| Example | Average diameter (nanometers) | polydispersion index |
|---------|-------------------------------|----------------------|
| 3a | 80 | 0.16 |
| 3b | 85 | 0.20 |
| 3c | 85 | 0.22 |

EXAMPLE 4 (Comparison)

450 mg of stearic acid and 100 mg of palmitic acid are melt-heated at about 65° C.

A mixture formed by 150 mg of purified egg lecithin, 190 mg of butyric acid and 110 mg of an aqueous solution (20 mg/ml) of LHRH is heated at the same temperature and mixed with the stearic and palmitic acids obtaining a clear microemulsion at a temperature about equal to 65° C.

Such microemulsion is added to a mixture consisting of sodium taurocholate (7.5 mg), egg lecithin (7.5 mg), butyric acid (7.5 mg), water (77 mg) and 9.5 mg of Rhodamine B heated at about 65° C. obtaining after dispersion in water and washing according to the Example 1) microparticles having an average diameter equal to 100 nm and a polydispersion index equal to 0.24.

EXAMPLE 5

The Example 4 has been repeated with the difference that in the second step (addition of the clear microemulsion to said mixture) dipalmitoyl phosphatidylethanolamine-PEG (DPPE-PEG) is also added respectively in the amounts equal to 0.25% (Example 5a), 0.35% (Example 5b) and 0.7% (Example 5c).

EXAMPLE 6

The Example 4 has been repeated with the difference that in the second step stearic-acid-PEG is added respectively in the amounts equal to 0.15% (Example 6a), 0.25% (Example 6b) and 0.60% (Example 6c).

What is claimed is:

1. A method of making a pharmaceutical composition containing a drug and solid lipidic microparticles which are suitable for parenteral administration, resistant to phagocytosis by macrophage, said method comprising adding one or more substances selected from the group consisting of dipalmitoyl phosphatidylethanolamine-PEG, and diacylphosphatidylethanolamines pegoylated with the methyl ether of polyethylene glycol.

2. The method of claim 1, wherein said microparticles have an average diamete r lower than one micrometer and a polydispersion index ranging from 0.10 to 0.50.

3. The method of claim 1, wherein said lipidic microparticles comprise a lipidic substance selected from the group consisting of trilaurin, tricapriloin, tristearin, tripalmitin, dipalmitin, distearin, lauric acid, myristic acid, palmitic acid, stearic acid, an d their esters and alcohols and polyalcohols, lauryl alcohol, myristic alcohol, cetyl alcohol, stearyl alcohol, cholesterol, cholesterylpalmitate, cholesterylbutyrate and cholesterylbenzoate.

4. The method as claimed in claim 1, wherein the content of said drug with respect to the lipidic substance ranges from 0.4 to 12% by weight.

5. The method as claimed in claim 1, wherein the content of said substance added to make said microparticles resistant to phagocytosis by macrophages, with respect to lipidic substance ranges from 0.8 to 8% by weight.

* * * * *